(12) United States Patent
Kawahara et al.

(10) Patent No.: US 8,168,618 B2
(45) Date of Patent: May 1, 2012

(54) EMULSIFYING AGENT

(75) Inventors: Hidehisa Kawahara, Suita (JP); Jun Tomono, Akashi (JP); Hiroaki Inoue, Kobe (JP); Hitoshi Obata, Suita (JP)

(73) Assignee: Kaneka Corporation, Osaka-Shi (JP)

( * ) Notice: Subject to any disclaimer, the term of this patent is extended or adjusted under 35 U.S.C. 154(b) by 494 days.

(21) Appl. No.: 12/087,586

(22) PCT Filed: Jan. 18, 2007

(86) PCT No.: PCT/JP2007/050706
§ 371 (c)(1),
(2), (4) Date: Sep. 25, 2008

(87) PCT Pub. No.: WO2007/083707
PCT Pub. Date: Jul. 26, 2007

(65) Prior Publication Data
US 2009/0035417 A1    Feb. 5, 2009

(30) Foreign Application Priority Data
Jan. 19, 2006    (JP) ................................. 2006-011407

(51) Int. Cl.
*A01N 45/00*    (2006.01)
*A61K 31/59*    (2006.01)

(52) U.S. Cl. .................................................. 514/167

(58) Field of Classification Search .................. None
See application file for complete search history.

(56) References Cited

U.S. PATENT DOCUMENTS

| 5,298,246 A | 3/1994 | Yano et al. |
| 6,426,078 B1 | 7/2002 | Bauer et al. |

FOREIGN PATENT DOCUMENTS

| EP | 0790316 A2 | | 8/1997 |
| EP | 0790316 A2 | * | 8/1997 |
| JP | 47/25220 B2 | | 10/1972 |
| JP | 52044781 | | 4/1977 |
| JP | 58-128141 A | | 7/1983 |
| JP | 60-199814 A | | 10/1985 |
| JP | 61-056124 A | | 3/1986 |
| JP | 61-260860 A | | 11/1986 |
| JP | 4-011935 A | | 1/1992 |
| JP | 4011935 | * | 1/1992 |
| JP | 19920116 | * | 1/1992 |
| JP | 4-299940 A | | 10/1992 |
| JP | 5-78240 | * | 3/1993 |
| JP | 5-78240 A | | 3/1993 |
| JP | 10-000098 A | | 1/1998 |
| JP | 10-263385 A | | 10/1998 |
| JP | 11-342326 A | | 12/1999 |

OTHER PUBLICATIONS

Cameron et al., The mannoprotein of *Saccharomyces cerevisiae* is an effective Bioemulsifier, Applied Environ. Microbiology 54, 1420-1425, 1988.*
Shimada et al., Increased carotenoid production by the food yeast *Candida utilis* through metabolic engineering of the isoprenoid pathway, Applied Environ. Microbiology 64, 2676, 1998.*
Cameron et al., The Mannoprotein of *Saccharomyces cerevisiae* Is an Effective Bioemulsifier, Applied Environ Microbiology 54: 1420-1425 (1988).*
Shimada et al., Increased Carotenoid Production by the Food Yeast *Candida utilis* through Metabolic Engineering of the Isoprenoid Pathway, Applied Environ Microbiology 64: 2676-2680 (1998).*
English translation of International Preliminary Report on Patentability (Chapter 1).
Partial English translation of JP S52-44781 which published on Apr. 8, 1977.
Partial English translation of JP-H4-11935 which published on Jan. 16, 1992.
Full English translation of JP-10-000098 which published on Jun. 1, 1998.
Full English translation of JP-11-342326-A which published on Dec. 14, 1999.
Full English translation of JP-5-78240-A which published on Mar. 30, 1993.
Full English translation of JP-10-263385-A which published on Oct. 6, 1998.

* cited by examiner

*Primary Examiner* — Johann Richter
*Assistant Examiner* — Thor Nielsen
(74) *Attorney, Agent, or Firm* — Birch, Stewart, Kolasch & Birch, LLP

(57) ABSTRACT

The present invention has its object to provide a novel emulsifier which is obtainable from an edible yeast and is highly safe and shows by itself a high level of emulsifying property and high emulsion stability; a water-soluble composition containing a liposoluble substance, together with the emulsifier; and methods of producing these. The present invention includes: an emulsifier which comprises, as an active ingredient, a carbohydrate- and protein-based complex derived from a culture fluid obtained by cultivating an edible yeast; a water-soluble composition which comprises an emulsifier and a liposoluble substance; and a method of producing the emulsifier and the water-soluble composition.

13 Claims, No Drawings

EMULSIFYING AGENT

TECHNICAL FIELD

The present invention relates to a novel emulsifier and a water-soluble composition. More particularly, it relates to an emulsifier which comprises an edible yeast-derived carbohydrate- and protein-based complex as an active ingredient used as an auxiliary agent in producing emulsions, the emulsions being a mixture of water and fats and/or oils, and also relates to a water-soluble composition obtained by using the emulsifier as well as methods of producing these.

BACKGROUND ART

Emulsifiers are, as substances essential to modern life, used in various production processes such as a production process of the so-called detergents, and are also contained in various articles for daily use and various food products. Alkyl sulfates obtained via organic synthetic routes, polyoxyethylene-based low-molecular-weight synthetic emulsifiers, etc. have so far been used as such emulsifiers. However, it has already been pointed out that these hardly undergo microbial degradation and, once they are released into the environment, they will not undergo biodegradation but be accumulated in the environment, possibly causing environmental pollution. Coating compositions and the like so far used in the form of solutions in organic solvents also have the possibility of causing similar environmental pollution and, from the occupational-safety viewpoint as well, it is desired that water be used in lieu of the solvents in current use.

To cope with such situation, it is necessary to provide coating compositions and the like with a certain degree of viscosity so that, for instance, in utilization of coating compositions and the like, sagging at coated sites after application thereof may be prevented. Since, however, the emulsifiers in conventional use are insufficient in viscosity, further addition of a thickening agent is required; this makes the compositions in question more complicated, causing problems in production and/or economic problems.

Also available as emulsifiers to be applied to mammals are such synthetic emulsifies as sugar esters. From the safety viewpoint, however, the utilization of natural products is desirable and, for example, proteins such as casein, lipids such as lecithin and plant polysaccharides such as gum arabic are utilized as natural emulsifiers. Although these are high in emulsifying property, the solutions thereof are low in viscosity and, when left for a long period of time, they disadvantageously separate into an aqueous phase and an oil phase. To solve this problem, it becomes necessary to add these emulsifiers in increased amounts or use them in combination with such a thickening agent as xanthan for stabilization; thus, they have problems from the economic and/or production viewpoint. Gum arabic has another problem; since it is a plant-derived product, the production thereof depends on the climatic conditions and the like, and therefore it is difficult to ensure a stable supply thereof.

According to other patent specifications in which the use of polyalcohols in emulsions containing a carotenoid or vitamin is described, it is necessary to additionally use an alcohol such as ethanol (cf. Patent Document 1), a nonionic emulsifier such as a polyglycerol fatty acid ester (cf. Patent Document 2), or both of them (cf. Patent Document 3). However, alcohols and nonionic emulsifiers are not favorably applicable in many preparations, in particular for mammals or, generally, they are not approved for use in foodstuffs. Further, a method is known for the production of carotenoid emulsions based on glycerol or another polyhydric alcohol and to be enclosed in soft gelatin capsules (cf. Patent Document 4). However, the emulsifiers used in the examples of the document are similarly nonionic emulsifiers and a further drawback is that the contents of active substances are relatively low.

Coenzyme Q10, which is one of coenzyme Q species and also known as ubidecarenone or CoQ10, is known as a liposoluble substance and technologies for retaining the homogenization and soluble condition thereof has been developed. For example, fat emulsions treated in a Manton-Gaulin high-pressure homogenizer using nonionic emulsifiers such as polyethylene glycol and polyoxyethylene-hydrogenated castor oil-(20)-ether have been disclosed (cf. Patent Document 5). Further, emulsions for intravenous injection given a particle diameter of 0.5 to 300 µm by treatment with a vegetable oil such as soybean oil or a phospholipid emulsifier such as phosphatidylcholine have been disclosed (cf. Patent Document 6). However, the former method has a problem in that the fat emulsions are large in particle diameter and inferior in transparency. Further, the latter emulsions for intravenous injection are low in coenzyme Q10 content and, when the concentration is increased, the problem of poor storage stability arises. As far as water-soluble compositions containing coenzyme Q10 are concerned, it is demanded that no oil component be necessary for emulsification and no special conditions or no complicated steps be required in the production.

In food manufacturing processes, there is a creaming phenomenon problem; when a liposoluble natural product is added to foods to be subjected to heat treatment in production steps such as cans, the emulsion is destructed and the liposoluble natural product floats up to the surface. In an attempt made to clear up this problem, a sucrose-condensed ricinoleic acid ester and an alcohol are used for heat-resisting emulsification (cf. Patent Document 7). However, in cases where the heating conditions are severe, for example, in the case of retort treatment of canned coffee (generally 125° C., 20 minutes), even the above prior-art technology allows the destruction of emulsions and the occurrence of creaming as a result. An emulsifier more resistant to heat is thus demanded.

In the field of cosmetics, emulsifiers are used especially for rendering liposoluble ingredients such as liposoluble colorants applicable smoothly over the skin and for dispersing them uniformly in cosmetics. In this case, chemically synthesized emulsifiers are in frequent use, and the possibility of their causing various troubles when they are used for a long period of time by direct application to the skin has been pointed out; thus, in the field of cosmetics as well, an emulsifier highly safe and friendly to the skin has been demanded.

Bath additives are mainly composed of: hot spring-derived inorganic salts; or an alkali carbonate and an organic acid with a perfume, a colorant, a plant extract, and the like are incorporated into a composition generating carbon-dioxide gas in the bath. In recent years, the skin-care effect of bathing has attracted increasing attention and a number of proposals for bath additives producing a skin-care effect have been offered. The methods of producing a skin-care effect by means of bath additives include: incorporation of moisturizing components such as polyhydric alcohols, polysaccharides or milk constituents; incorporation of plant extracts alleged to have a skin-care effect; and incorporation of oils, for instance. However, water-soluble moisturizing components are dissolved in bath water to give a dilute solution, and therefore hardly remain on the skin, hence their effect is weak. The use thereof in increased amounts so that their effect can be expected may make the skin after bathing sticky and, in addition, is uneconomical, hence is inexpedient. On the contrary, the use of oils is an effective means for producing an effect and giving a feeling of use by using relatively small amounts and, generally, the type of bath additives is such that oils are emulsified in bath water by means of an emulsifier. However, there is a limit to the level of incorporation of oils; excessive addition levels make the preparations inferior in fluidity and cause troubles in making preparations and, therefore, an emulsifier effective at lower addition levels is required. On the occasion of bathing, water is used in large amounts and an emulsifier is required also in large amounts, so that a safety problem will presumably arise; therefore, a highly safe emulsifier is demanded.

For such reasons as mentioned above, nature-derived emulsifiers higher in safety than in the prior art are required. Thus, such biological material-derived emulsifiers as mentioned below have been reported. A substance resulting from fusion between mannose and a protein is contained in the cell wall of Saccharomyces cerevisiae and this is known to show emulsifying action (cf. Non-Patent Document 1). For preparing this substance in this case, cells must be disrupted and the procedure therefor is very troublesome; accordingly, the substance has not been put to practical use as yet. Candida lipolytica isolated from the environment by screening is known to produce, in the medium, a substance showing emulsifying action (cf. Non-Patent Document 2). In cultivating this species, the use of such a hardly soluble carbon source as hexadecane is required, whereas the substance obtained by using such a soluble carbon source as glucose shows only low emulsifying action; this is a drawback.

Such substances obtained from the culture fluids of microorganisms and having emulsifying action are called biosurfactants, and are advantageous because they are neither toxic to living organisms nor persistent in the environment. They can also be mass-produced by cultivation. However, while the safety of these biosurfactants is said to be high, the fungi producing them are originally obtained from the environment, for example soils or woods, by screening with the ability to highly utilize oils, for instance, as an indicator, that is, those materials have never been eaten by humans; therefore, such biosurfactants can hardly be said to be truly high in safety. Known as emulsifiers derived from yeasts which have been eaten by mankind are emulsifiers derived from yeasts belonging to the genus Saccharomyces or Kluyveromyces (cf. Patent Document 8). These are, however, obtained only after heat treatment of cells themselves and are not defined as ones obtained from culture fluids.

In the natural world, there exist various microorganisms and, among them, there are some having an unknown function and biosurfactant-producing fungi have also been reported, and a certain number of biosurfactants such as surfactins and rhamnolipids (cf. Non-Patent Document 3) and sophorolipids (cf. Non-Patent Document 4) have already been put to practical use as a result of increases in productivity thereof. However, these biosurfactant producers are fungi isolated from the environment, typically soils, and whether they have actually been eaten by mankind or not is unknown; hence, they can hardly be said to be truly safe. Among the biosurfactants known in the art, sophorolipids are yeast-derived ones; however, they are of the glycolipid type from the surfactant-classification viewpoint, and the producers thereof, namely *Candida bombicola*, are taxonomically different from the yeast species to be used in the practice of the present invention and are not ones isolated from sources which have been eaten by mankind.

Patent Document 1: Japanese Kokai Publication S47-25220

Patent Document 2: Japanese Kokoku Publication S61-260860

Patent Document 3: Japanese Kokoku Publication S60-000419

Patent Document 4: Japanese Kokoku Publication S58-128141

Patent Document 5: Japanese Kokai Publication S60-199814

Patent Document 6: Japanese Kokai Publication S61-56124

Patent Document 7: Japanese Kokai Publication H04-299940

Patent Document 8: Japanese Kokai Publication H10-98

Non-Patent Document 1: D. R. Cameron et al., Applied and Environmental Microbiology, June 1988, 54, 6: p. 1420-1425

Non-Patent Document 2: M. C. Cirigliano et al., Applied and Environmental Microbiology, October 1984, p. 747-750

Non-Patent Document 3: M. Benincasa et al., 2002, J. Food Eng., 54: 283-288

Non-Patent Document 4: M. Deshpande and L. Daniels, 1995, Bioresour. Technol., 53: 143-150

SUMMARY OF THE INVENTION

It is an object of the present invention to solve the above problems and to provide a novel emulsifier which is obtainable from an edible yeast and is highly safe and shows by itself a high level of emulsifying property and emulsifying stability; a water-soluble composition containing a liposoluble substance, together with the emulsifier; and methods of producing these.

The present inventors made intensive investigations in an attempt to accomplish the above object and, as a result, found that when a carbohydrate- and protein-based complex in an edible yeast-derived culture fluid is added to a liposoluble substance-containing solution, the liposoluble substance can be stably emulsified by homogenizing the same and the resulting emulsion remains stable for a long period of time even after heat treatment. Based on such finding, the present invention has now been completed.

That is, the present invention relates to an emulsifier which comprises, as an active ingredient, a carbohydrate- and protein-based complex derived from a culture fluid obtained by cultivating an edible yeast.

Also, the present invention relates to a water-soluble composition which comprises the emulsifier and a liposoluble substance.

Further, the present invention relates to a method of producing an emulsifier, wherein an edible yeast is cultivated and a carbohydrate- and protein-based complex fraction is separated and recovered from the culture fluid obtained.

Further, the present invention relates to a method of producing a water-soluble composition, wherein the emulsifier and a liposoluble substance are mixed with each other.

DETAILED DESCRIPTION OF THE INVENTION

In the following, the present invention is described in detail.

First, the emulsifier according to the present invention comprises, as an active ingredient, a carbohydrate- and protein-based complex in a culture fluid obtained by cultivating an edible yeast.

The edible yeast to be used in the practice of the present invention is not particularly restricted in genus or species but may be any edible yeast capable of producing a carbohydrate- and protein-based complex. The edible yeast is different from Rhodotorula.

As the edible yeast, there may be mentioned: baker's yeasts used for bread dough fermentation; wine yeasts used in wine-making; sake yeasts used in sake brewing; brewer's yeasts used in beer brewing; shochu yeasts used in shochu brewing, and mirin yeasts used in mirin brewing. Among them, yeasts used in producing such alcohol-containing products as wine, sake, beer, shochu and mirin, which are classified as yeasts for brewing, are preferred.

Preferably used as the edible yeast in the practice of the present invention are edible yeasts of the genera *Candida* and *Saccharomyces* because they can be cultivated with ease and can be grown using inexpensive materials as nutrient sources. More specifically, *Candida* sake, *Saccharomyces* sake, *Saccharomyces cerevisiae* and the like are more preferably used.

Among those edible yeasts, such yeasts for brewing as *Candida* sake NBRC1213, *Candida* sake NBRC0435 and *Saccharomyces* sake Kyokai No. 10; and such baker's yeasts as *Saccharomyces cerevisiae* NBRC0538, *Saccharomyces cerevisiae* NBRC0853 and *Saccharomyces cerevisiae* ATCC9018 are still more preferably used because these can produce substances having emulsifying action in large amounts. In particular, *Candida* sake NBRC1213 and *Saccharomyces* sake Kyokai No. 10 are preferably used.

*Candida* sake NBRC1213, *Candida* sake NBRC0435, *Saccharomyces* cerevisiae NBRC0538 and *Saccharomyces cerevisiae* NBRC0853 are available from NBRC (National Institute of Technology and Evaluation (NITE) Department of Biotechnology Biological Resource Center). Saccharomyces sake Kyokai No. 10 is available from Brewing Society of Japan. Further, *Saccharomyces cerevisiae* ATCC9018 is available from ATCC (The American Type Culture Collection).

Those edible yeasts may be used singly or two or more of them may be used in combination.

Those edible yeasts can be cultivated with ease and have properties suited for large-scale cultivation to produce aggregation-inhibiting substances. Thus, those edible yeasts can grow steadily in a medium comprising inorganic salts with glucose used as a carbon source, and the fraction in culture fluids which can be precipitated and concentrated with ethanol, hexane, acetone, etc. (the fraction containing a carbohydrate- and protein-based complex) has potent aggregation-inhibiting activity.

As for the method of cultivation, the edible yeasts can be cultivated in a medium generally used for cultivating microorganisms. Glucose is preferably used as the carbon source contained in the medium and necessary for the growth of edible yeasts. The concentration thereof is preferably about 0.1 to 5% by volume, more preferably about 0.5 to 1.5% by volume.

On that occasion, an alcohol such as ethanol or an oil such as corn oil or soybean oil may also be used as the carbon source in lieu of or in combination with glucose.

Ammonium salts are preferably used as the nitrogen source and, in particular, ammonium phosphate is preferred from the viewpoints of the pH-buffering action and phosphorus supplementation.

With the progress of cultivation, the pH of the medium lowers, so that the cultivation is preferably carried out while adjusting the medium to pH 6 to 8, more preferably pH 6.5 to 7.5, by dropwise addition of an alkali.

On that occasion, any alkali such as sodium hydroxide, potassium hydroxide, ammonia and an amine compound may be used. For supplementing a nitrogen source for the growth of cells, however, ammonia is preferably used.

For supplementing the medium with vitamins and the like, a yeast extract may be added. Since the carbon source glucose gradually decreases with the growth of cells, it is necessary to supplement the same consecutively and, on this occasion, it is also possible to add a mixture of ammonia and ethanol. Employable as the method of addition is the method comprising intermittent addition of a certain amount at each time, the method comprising continuous addition, or any other appropriate method.

The cultivation temperature is generally 10 to 45° C., more preferably around 20 to 35° C., from the viewpoint of the cell-growth rate.

The cultivation can be carried out in the manner of stirring culture or stationary culture, either with aeration or in a closed system. For accelerating the growth of the edible yeast, however, stirring culture under aeration is preferred. It is also possible to recover yeast cells and cause them to efficiently produce the desired emulsifier in the resting condition.

A fraction containing a carbohydrate- and protein-based complex and, further, the carbohydrate- and protein-based complex are separated and recovered from the culture fluid obtained by cultivation in the above manner. Prior to the separation and recovery, the edible yeast cells may be removed in advance from the culture fluid by centrifugation, for instance; it is also possible to use the culture supernatant.

Available for the separation and recovery of the carbohydrate- and protein-based complex are the method which comprises using such a quaternary amine as cetylpyridinium chloride or cetyltributylammonium bromide and the method which comprises adding a lower alcohol such as ethanol, methanol and isopropanol, or acetone. The former method is preferred for obtaining higher purity products, while the latter method is preferred for obtaining products more quickly. Both the methods may also be used in combination; the order thereof is optional.

The carbohydrate- and protein-based complex separated and recovered in the manner mentioned above is dried in the conventional manner for utilization as a powder, or the powder is again dissolved in a solvent such as water for utilization in the form of an aqueous solution, for instance.

It is also possible to separate and recover the complex by affinity-based fractionation using an ion exchange column, an affinity column, etc., or further, by molecular weight-based fractionation such as ultrafiltration or the use of a gel filtration column.

The carbohydrate- and protein-based complex to be contained as an active ingredient in the emulsifier according to the present invention is not particularly restricted but may be any carbohydrate- and protein-based complex obtained by cultivating any of the edible yeasts mentioned above.

The carbohydrate- and protein-based complex, which is produced in the culture fluid, shows remarkable emulsifying activity and can be easily separated from the edible yeast cells on the occasion of recovery of the carbohydrate- and protein-based complex from the culture fluid after production thereof by the edible yeast.

The carbohydrate- and protein-based complex can be used in the form secreted from the edible yeast cells into the culture fluid as a result of cultivation of the edible yeast. It can also be utilized in the form remaining in the yeast cells before secretion thereof.

The carbohydrate- and protein-based complex is not particularly restricted but refers to glycoproteins resulting from binding of a carbohydrate to a protein or a group of substances resulting from addition of a lipid, for instance, to such glycoproteins. The carbohydrate refers to one or more oligosaccharides and further includes structures resulting from repetitions of a specific carbohydrate as well. The protein moiety is composed of two or more amino acids.

The carbohydrate- and protein-based complex to be used may comprise a single species or two or more species.

The carbohydrate- and protein-based complex preferably has an average molecular weight of not lower than 100,000, more preferably not lower than 120,000.

While the average molecular weight can be determined in the conventional manner, for example using a laser scatterometer or by gel filtration, the data reported herein were determined by the gel filtration method as described later in the example section. Thus, the average molecular weight can be determined by providing the carbohydrate- and protein-based complex for a gel-filtration carrier and making a calculation based on a molecular-weight calibration curve prepared using a standard polymer kit. For example, the average molecular weight can be calculated by providing the carbohydrate- and protein-based complex obtained for a gel-filtration carrier (Sephacryl S-400, product of Amersham Biosciences, φ10 mm×length 100 cm) using a molecular-weight calibration curve with a standard polymer kit (product of TOSOH CORPORATION).

The emulsifier according to the present invention comprises, as an active ingredient, the carbohydrate- and protein-based complex produced by the edible yeast mentioned above. The edible-yeast culture fluid containing the carbohydrate- and protein-based complex produced may be used as such, or the carbohydrate- and protein-based complex may be used in the form purified (=separated and recovered).

In particular when the emulsifier is used in small amounts, it is effective to purify the same because the concentration of the carbohydrate- and protein-based complex in the emulsifier can be increased.

Furthermore, for utilizing the carbohydrate- and protein-based complex remaining in yeast cells, it is also possible to use the yeast cells as such or to utilize the cell-disruption fluid.

As other components in the emulsifier, there may be mentioned the edible-yeast culture-fluid components other than the carbohydrate- and protein-based complex, such as mentioned above; it is also possible to use one or more of various additives to increase the effect of the emulsifier.

Usable as the additives are stabilizers for retaining the formulation of the emulsifier and/or preventing the carbohydrate- and protein-based complex from decomposing to decrease the effect thereof, and liquids such as water for facilitating the actual use thereof. The emulsifier may also contain, as additives, one or more of antioxidants, preservatives, cosmetic active agents, moisturizers, sphingolipids, liposoluble polymers, and the like.

Furthermore, the emulsifier according to the present invention can also be used in combination with existing emulsifiers.

The levels of addition of such additives and such existing emulsifiers may be properly selected according to the intended use thereof.

The emulsifier formulation may be either liquid or solid. For attaining uniform mixing of the emulsifier with a liposoluble substance in contacting with the liposoluble substance, however, the liquid form is preferred.

The emulsifier production method according to the present invention is a method in which an edible yeast is cultivated and a fraction containing a carbohydrate- and protein-based complex in the culture fluid obtained is separated and recovered, and the particulars thereof are as mentioned hereinabove.

It is preferable to obtain a fraction with a molecular weight of not lower than 100,000, more preferably not lower than 120,000, determined by gel filtration by separating and recovering the fraction containing the carbohydrate- and protein-based complex.

The molecular weight of the fraction containing the carbohydrate- and protein-based complex can be determined by such a gel filtration method as described later in the example section.

The water-soluble composition containing a liposoluble substance is now described; the water-soluble composition is obtainable by using the emulsifier comprising the above-mentioned carbohydrate- and protein-based complex produced by an edible yeast in the above manner and contacting the same with a liposoluble substance.

Thus, the water-soluble composition according to the present invention contains the above-mentioned emulsifier and the liposoluble substance.

The liposoluble substance to be used in the practice of the present invention is not particularly restricted but may be any of those which are physiologically acceptable, for example, liposoluble drugs such as coenzyme Q10; vitamins such as liposoluble vitamins A, D, E and K and derivatives thereof; fats and oils such as essential oils (e.g. pine oil, lime oil, citrus oil, etc.), vegetable oils (e.g. soybean oil, rapeseed oil, safflower oil, corn oil, sesame oil, cottonseed oil, olive oil, palm oil, sunflower oil, etc.), animal oils (e.g. beef tallow, lard, etc.), liposoluble colorants (e.g. annatto, turmeric, Monascus, chlorophyll, etc.), perfumes (e.g. orange oil etc.) and carotenoids (e.g. canthaxanthin, astaxanthin, zeaxanthin, lycopene, apocarotenal, β-carotene, etc.).

Such liposoluble substances may be used singly or two or more of them may be used in combination.

The water-soluble composition according to the present invention may contain various ingredients such as those additives exemplified above referring to the emulsifier, as well as pigments, seasonings, antimicrobials and so forth and can be provided with various performance as industrial products such as foodstuffs, cosmetics and bath additives.

In the water-soluble composition, there may favorably be incorporated a solvent such as water and an alcohol, for example ethanol.

The content of the carbohydrate- and protein-based complex in the water-soluble composition is not particularly restricted but preferably is 0.000001 to 10% by weight, more preferably 0.0001 to 1% by weight, based on the whole water-soluble composition.

The water-soluble composition production method according to the present invention is a method in which the above-mentioned emulsifier is mixed with a liposoluble substance.

In producing the water-soluble composition, the liposoluble substance and emulsifier are brought into contact with each other and the both are mixed up. The mixing method is not particularly restricted as long as both can be brought into sufficient contact with each other, for example, by shaking or stirring. For attaining rapid and sufficient miscibility of such a substance having relatively high viscosity as a liposoluble substance, stirring is preferred and, further, on the occasion of stirring, vigorous stirring is more preferred. Utilizable as such method of mixing the emulsifier with a liposoluble substance are such conventional methods as the method using a whirling blender or juicer, the method using a Manton-Gaulin homogenizer, and the method utilizing ultrasonic waves.

As regards the conditions in bringing the liposoluble substance and emulsifier into contact with each other and further mixing up the both, it is necessary to take into consideration the treatment temperature, treatment time and other factors. Generally, however, such contacting and mixing may be carried out under conditions properly selected according to the kind of the liposoluble substance employed and the intended use of the water-soluble composition containing the liposoluble substance to be obtained.

For example, when a material not very high in thermal stability is used, it is necessary to carry out mixing while care is taken to avoid elevated temperatures, because heat may be generated during mixing. Specifically, in the case of application to foodstuffs and the like and in the case of application to coating compositions and others containing a volatile solvent and the like, it is necessary to finish the mixing process in a short period of time so that microorganisms may not propagate in the former case or the solvent may not volatilize in the latter case.

In adding the emulsifier to the liposoluble substance, all possible modes of addition may be employed; for example, both may be added to each other all at once and then mixed up together, or both may be added to each other gradually in small portions while mixing up together, or one may be added gradually to the other while mixing up together.

EFFECTS OF THE INVENTION

The present invention can provide a novel emulsifier which is highly safe and by itself shows high emulsifying property and high emulsion stability. A water-soluble composition containing a liposoluble substance stably emulsified therein can be obtained using the emulsifier. Thus, the industrial contribution of the present invention is very great.

BEST MODE FOR CARRYING OUT THE INVENTION

The following examples illustrate the present invention in further detail. They are, however, by no means limitative of the scope of the present invention.

Example 1

Preparation of Crude Emulsifier Derived from Yeast Culture Fluid

YM medium (containing per liter: 3.0 g of a yeast extract; 3.0 g of a malt extract; 5.0 g of peptone; and 10 g of glucose) was prepared and sterilized by autoclaving. Then, this medium was distributed into 10 tubes by 4 ml each and inoculated with Candida sake NBRC1213, followed by overnight cultivation at 26° C. with stirring at 160 rpm to give preculture fluids. The main culture was carried out according to the following procedure. The above medium was distributed into ten 2-liter Sakaguchi flasks by 400 ml each and sterilized by autoclaving. The medium in each flask was inoculated with 4 ml of the above preculture fluid. After 5-days cultivation at 25° C. with stirring at 100 rpm, the culture fluid was centrifuged at 10,000×g for 20 minutes, and about 4 liters of a yeast cell-free supernatant was recovered. This supernatant (about 4 liters) was concentrated to about 450 ml using an ultrafiltration membrane with a cut-off value MW of 3,000. Then, the concentrate was dialyzed against a buffer A [20 mM Tris hydrochloride buffer (pH 7.5)] to give a crude emulsifier.

Example 2

Evaluation of Emulsifying Action (1) In the Case of Kerosene Being Used as a Target Substance in Evaluation of Emulsifying Action In tubes (products of Iwaki Co., Ltd., φ12 mm×75 mm, made of polypropylene), there were placed the crude emulsifier prepared in Example 1 or dilutions thereof in the following dilution factors: a) 1.0 ml of the crude emulsifier; b) 0.5 ml of the crude emulsifier plus 0.5 ml of the buffer A; and c) 0.1 ml of the crude emulsifier plus 0.9 ml of the buffer A, and 1.0 ml of kerosene (product of Wako Pure Chemical Industries, Ltd.) was added to each tube. In a control run, about 10-fold concentrated YM medium using an ultrafiltration membrane with a cut-off value MW of 3,000 was used. Each mixture was stirred on a vortex mixer (product of Scientific Industries, Inc.) set at the maximum level for 2 minutes and then allowed to stand for 24 hours. Thereafter, the volumes of the emulsified layers were measured and found to be a) 1.7 $cm^3$, b) 1.4 $cm^3$ and c) 1.1 $cm^3$; thus, the emulsified layer obtained increased in volume (indicating an increased extent of emulsification) with the increase in the proportion of the crude emulsifier. In the case of the concentrated YM medium used as the control, the aqueous and oily layers separated from each other and no emulsified layer was observed.

(2) In the Case of Astaxanthin Being Used as a Liposoluble Substance

Astaxanthin (10 μl thereof was dissolved in dimethyl sulfoxide to be a 2 mg/ml solution; product of Wako Pure Chemical Industries, Ltd.) was added to 90 μl of the buffer A, and 100 μl of the crude emulsifier prepared in Example 1 was added thereto, followed by thorough mixing. In a control run, a preparation produced in the same manner as in Example 1 from a culture fluid derived from Saccharomyces cerevisiae NBRC223 having no experience of being eaten by mankind was used. Upon observation over 24 hours while allowing to stand at 25° C., astaxanthin began to precipitate out after the lapse of about 1 hour and the whole amount thereof precipitated out in 24 hours in the control run. On the contrary, no aggregation was observed at all even after the lapse of 24 hours in the case of addition of the crude emulsifier. Further, the mixture of the crude emulsifier and astaxanthin was allowed to stand at room temperature for 1 week; no aggregate precipitation was observed.

Example 3

Partial Purification of Substance Having Emulsifying Action and Properties Thereof The crude emulsifier prepared in Example 1 was applied to a column (φ2.5 cm×25 cm) packed with 125 ml of an anion-exchange resin DEAE-TOYOPEARL 650M (product of TOSOH CORPORATION) equilibrated in advance with the buffer A, followed by elution by the linear concentration gradient method (from 0 to 1.0 M sodium chloride; total eluate volume 1500 ml). About 60 ml of a fraction having emulsifying activity (substance having emulsifying action) eluted at sodium-chloride concentrations around 200 mM was recovered. This was dialyzed against the buffer A, and the dialyzate was used as a roughly purified sample in the experiments (1) and (2) described below. The emulsifying activity was evaluated in terms of kerosene-emulsifying action as in Example 2.

(1) A 600 U/ml solution of proteinase K (product of Takara Bio Inc.) was prepared, and this was mixed with the above-mentioned roughly purified sample in a protein quantity ratio of 1:9 (final proteinase K concentration 6 U/ml) and the mixture was maintained at 37° C. for 22 hours. Using this fraction having emulsifying activity, the emulsifying action thereof was observed in the same manner as in Example 2; the emulsifying action had disappeared. The intensity of the activity of each fraction obtained in this DEAE purification process was proportional to the intensity of the absorption of the carbohydrate. In view of these facts, the substance having emulsifying action was considered to be a carbohydrate- and protein-based one.

(2) A 100-μl portion of the above roughly purified sample was added to 0.9 ml of 10-mM potassium-phosphate buffer (pH 7.0), and the mixture was further added to 10 mg of β-carotene (product of Nacalai Tesque, Inc.), vitamin A (product of Nacalai Tesque, Inc.), vitamin E (product of Nacalai Tesque, Inc.), vitamin K1 (product of Nacalai Tesque, Inc.) and coenzyme Q10, respectively, and each mixture was thoroughly mixed. As a result, each solid was dispersed in the liquid. In a control run in which water was used, each of these substances was found in a state floating on the liquid surface.

Example 4

Measurement of Substance Having Emulsifying Action for Molecular Weight

A 30-ml portion of the roughly purified sample obtained in Example 3 was concentrated to 2 ml with polyethylene glycol (polyethylene glycol 20,000, product of Wako Pure Chemical Industries, Ltd.), the concentrate was provided for a gel filtration carrier (HiLoad 16/60 Superdex 200, φ1.6 cm×length 60 cm), and a fraction having a molecular weight of 120,000 or higher and showing emulsifying activity was recovered and lyophilized to give about 0.3 g of a sample. Further, using this sample, gel filtration was carried out on a gel filtration carrier (Sephacryl S-400, product of Amersham Biosciences, φ10 mm×length 100 cm) and the molecular weight thereof was calculated using a molecular-weight calibration curve with a standard polymer kit (product of TOSOH CORPORATION) and was found to be about 190,000.

Example 5

Structure Estimation

The sample after gel filtration as obtained in Example 4 was lyophilized, the lyophilization product was dissolved in distilled water, and the solution was subjected to carbohydrate-content determination by the phenol-sulfuric acid method and to protein-moiety quantitation by the BCA method (protein moiety). As a result, the carbohydrate/protein ratio was calculated and found to be about 10:1. Further, the sample was hydrolyzed in the presence of 2-M sulfuric acid at 100° C. for 3 hours and then neutralized, and the thus-obtained sample was subjected to constituent-carbohydrate analysis by high-performance liquid chromatography (TOSOH CORPORATION's system for the analysis of reducing carbohydrate), upon which mannose was detected. This result revealed that the carbohydrate moiety contains mannose.

Example 6

Preparation of Crude Emulsifier Derived from Yeast Culture Fluid

YM medium (containing per liter: 3.0 g of a yeast extract; 3.0 g of a malt extract; 5.0 g of peptone; and 10 g of glucose) was prepared and sterilized by autoclaving. Then, this medium was distributed into 10 tubes by 4 ml each, and inoculated with Saccharomyces sake Kyokai No. 10 (sake yeast), followed by one-day cultivation at 28° C. with stirring at 160 rpm to give preculture fluids. The main culture was carried out according to the following procedure. Ten-fold concentrated YNB medium (product of DIFCO) was distributed into ten 2-liter Sakaguchi flasks by 400 ml each and sterilized by autoclaving. The medium in each flask was inoculated with 4 ml of the above preculture fluid. After 7-days cultivation at 30° C. with stirring at 100 rpm, the culture fluid was centrifuged at 9,000×g for 10 minutes, and about 4 liters of a yeast cell-free supernatant was recovered. This supernatant (about 4 liters) was concentrated to about 500 ml using an ultrafiltration membrane with a cut-off value MW of 20,000 (crude emulsifier A). Then, the sample was fed to a dialysis membrane and concentrated to 50 ml using polyethylene glycol (PEG 20,000, product of Wako Pure Chemical Industries, Ltd.). Thereafter, the concentrate was dialyzed against the buffer A [20 mM Tris hydrochloride buffer (pH 7.5)] to give a crude emulsifier B.

Example 7

Evaluation of Emulsifying Action (1) In the Case of Kerosene Being Used as a Target Substance in Evaluation of Emulsifying Action In tubes (products of Iwaki Co., Ltd, φ12 mm×75 mm, made of polypropylene), there were placed the crude emulsifier A prepared in Example 6 or dilutions thereof in the following dilution factors: a) 1.0 ml of the crude emulsifier; b) 0.5 ml of the crude emulsifier A plus 0.5 ml of the buffer A; and c) 0.1 ml of the crude emulsifier A plus 0.9 ml of the buffer A, and 1.0 ml of kerosene (product of Wako Pure Chemical Industries, Ltd.) was added to each tube. In a control run, about 10-fold concentrated YM medium using an ultrafiltration membrane with a cut-off value MW of 20,000 was used. Each mixture was stirred on a vortex mixer (product of Scientific Industries, Inc.) set at the maximum level for 2 minutes and then allowed to stand for 24 hours. Thereafter, the volumes of the emulsified layers were measured and found to be a) 1.6 cm$^3$, b) 1.2 cm$^3$ and c) 0.9 cm$^3$; thus, the emulsified layer obtained increased in volume (indicating an increased extent of emulsification) with the increase in the proportion of the crude emulsifier. In the case of the concentrated YM medium used as the control, the aqueous and oily layers separated from each other and no emulsified layer was observed.

(2) In the Case of Astaxanthin Being Used as a Liposoluble Substance

Astaxanthin (10 μl thereof was dissolved in dimethyl sulfoxide to be a 2 mg/ml solution; product of Wako Pure Chemical Industries, Ltd.) was added to 90 μl of the buffer A, and 100 μl of the crude emulsifier A prepared in Example 6 was added thereto, followed by thorough mixing. In a control run, the same culture fluid derived from Saccharomyces cerevisiae NBRC223 having no experience of being eaten by mankind as used in Example 2 (2) was used. Upon observation over 24 hours while allowing to stand at 25° C., astaxanthin began to precipitate out after the lapse of about 1 hour and the whole amount thereof precipitated out in 24 hours in the control run. On the contrary, no aggregation was observed at all even after the lapse of 24 hours in the case of addition of the crude emulsifier. Further, the mixture of the crude emulsifier and astaxanthin was allowed to stand at room temperature for 1 week; no aggregate precipitation was observed. Thus, the addition of the crude emulsifier inhibited astaxanthin from aggregating.

Example 8

Partial Purification of Substance Having Emulsifying Action and Properties Thereof The crude emulsifier B prepared in Example 6 was applied to a column ($\phi$2.5 cm×25 cm) packed with 125 ml of an anion exchange resin DEAE-TOYOPEARL 650M (product of TOSOH CORPORATION) equilibrated in advance with the buffer A, followed by elution by the linear concentration gradient method (from 0 to 1.0 M sodium chloride; total eluate volume 1000 ml). About 250 ml of a fraction having emulsifying activity (substance having emulsifying action) eluted at sodium chloride concentrations around 200 mM was recovered. This was dialyzed against the buffer A, and the dialyzate was used as a roughly purified sample in the experiments (1) and (2) described below. The emulsifying activity was evaluated in terms of kerosene-emulsifying action as in Example 7.

(1) A 600 U/ml solution of proteinase K (product of Takara Bio Inc.) was prepared, and this was mixed with the above-mentioned roughly purified sample in a protein quantity ratio of 1:9 (final proteinase K concentration 6 U/ml) and the mixture was maintained at 40° C. for 24 hours. Using this fraction having emulsifying activity, the emulsifying action thereof was observed in the same manner as in Example 7; the emulsifying action had disappeared. The intensity of the activity of each fraction obtained in this DEAE purification process was proportional to the intensity of the absorption of the carbohydrate. In view of these facts, the substance having emulsifying action was considered to be a carbohydrate- and protein-based one.

(2) A 100-µl portion of the above roughly purified sample was added to 0.9 ml of 10 mM potassium phosphate buffer (pH 7.0), and the mixture was further added to 10 mg of β-carotene (product of Nacalai Tesque, Inc.), vitamin A (product of Nacalai Tesque, Inc.), vitamin E (product of Nacalai Tesque, Inc.), vitamin K1 (product of Nacalai Tesque, Inc.) and coenzyme Q10, respectively, and each mixture was thoroughly mixed. As a result, each solid was dispersed in the liquid. In a control run in which water was used, each of these substances was found in a state floating on the liquid surface. Thus, the addition of this roughly purified sample resulted in increases in the dispersibility of these liposoluble substances in the aqueous solution.

Example 9

Measurement of Substance Having Emulsifying Action for Molecular Weight

A 250-ml portion of the roughly purified sample obtained in Example 8 was concentrated to 2 ml with polyethylene glycol (polyethylene glycol 20,000, product of Wako Pure Chemical Industries, Ltd.), and the concentrate was provided for a gel filtration carrier (HiLoad 16/60 Superdex 200, $\phi$1.6 cm×length 60 cm) and eluted with 0.15 M NaCl/25 mM TrisHCl (pH 7.5). A fraction having a molecular weight of 100,000 to 500,000 and showing emulsifying activity was recovered, dialyzed against distilled water, and lyophilized to give about 0.3 g of a sample. The molecular weight of this sample was calculated using a molecular-weight calibration curve with the Gel Filtration Calibration Kit HMW (product of GE Healthcare Biosciences) and was found to be about 300,000.

Example 10

Structure Estimation

The sample after gel filtration as obtained in Example 9 was lyophilized, the lyophilization product was dissolved in distilled water and hydrolyzed in the presence of 2-N sulfuric acid at 100° C. for 4 hours and then neutralized, and the thus-obtained sample was subjected to constituent-carbohydrate analysis by high-performance liquid chromatography (TOSOH CORPORATION's system for the analysis of reducing carbohydrate), upon which mannose was detected. This result revealed that the carbohydrate moiety contains mannose.

Example 11

Preparation of Crude Emulsifier Derived from Yeast Culture Fluid

YM medium (containing per liter: 3.0 g of a yeast extract; 3.0 g of a malt extract; 5.0 g of peptone; and 10 g of glucose) was prepared and sterilized by autoclaving. Then, this medium was distributed into 10 tubes by 4 ml each and inoculated with Saccharomyces cerevisiae NBRC0538, NBRC0853 or ATCC9018, followed by 2-days cultivation at 28° C. with stirring at 160 rpm to give preculture fluids. The main culture was carried out according to the following procedure. The above medium was distributed into 500-ml Sakaguchi flasks by 100 ml each, and sterilized by autoclaving. The medium in each flask was inoculated with 1 ml of the above preculture fluid. After 2-days cultivation at 28° C. with stirring at 100 rpm, the culture fluid was centrifuged at 10,000×g for 20 minutes, and about 4 liters of a yeast cell-free supernatant was recovered. A 100-ml portion of this supernatant was concentrated to about 10 ml using an ultrafiltration membrane with a cut-off value MW of 3,000. Thereafter, the concentrate was dialyzed against the buffer A [20 mM Tris hydrochloride buffer (pH 7.5)] to give a crude emulsifier C (NBRC0538), D (NBRC0853) and E (ATCC9018).

Example 12

Evaluation of Emulsifying Action (1) In the Case of Kerosene Being Used as a Target Substance in Evaluation of Emulsifying Action In tubes (products of Iwaki Co., Ltd, $\phi$12 mm×75 mm, made of polypropylene), there were placed the crude emulsifier C, D or E prepared in Example 11 or dilutions thereof in the following dilution factors: a) 1.0 ml of the crude emulsifier; b) 0.5 ml of the crude emulsifier plus 0.5 ml of the buffer A; and c) 0.1 ml of the crude emulsifier plus 0.9 ml of the buffer A, and 1.0 ml of kerosene (product of Wako Pure Chemical Industries, Ltd.) was added to each tube. In a control run, about 10-fold concentrated YM medium using an ultrafiltration membrane with a cut-off value MW of 3,000 was used. Each mixture was stirred on a vortex mixer (product of Scientific Industries, Inc.) set at the maximum level for 2 minutes and then allowed to stand for 24 hours. Thereafter, the volumes of the emulsified layers were measured and found to be a) 1.9 cm$^3$, b) 1.2 cm$^3$ and c) 1.0 cm$^3$ for the crude emulsifier C; a) 1.5 cm$^3$, b) 1.0 cm$^3$ and c) 0.8 cm$^3$ for the crude emulsifier D; and a) 1.3 cm³, b) 1.0 cm³ and c) 0.9 cm³ for the crude emulsifier E; thus, the emulsified layer obtained increased in volume (indicating an increased extent of emulsification) with the increase in the proportion of each crude emulsifier. In the case of the concentrated YM medium used as the control, the aqueous and oily layers separated from each other and no emulsified layer was observed.

(2) In the Case of Astaxanthin Being Used as Liposoluble Substance

Astaxanthin (10 µl thereof was dissolved in dimethyl sulfoxide to be a 2 mg/ml solution; product of Wako Pure Chemical Industries, Ltd.) was added to 90 µl of the buffer A, and 100 µl of the crude emulsifiers C, D or E prepared in Example 11 was added thereto, followed by thorough mixing. In a control run, the same culture fluid derived from Saccharomyces cerevisiae NBRC223 having no experience of being eaten by mankind as used in Example 2 (2) was used. Upon observation over 24 hours while allowing to stand at 25° C., astaxanthin began to precipitate out after the lapse of about 1 hour and the whole amount thereof precipitated out in 24 hours in the control run. On the contrary, no aggregation was observed at all even after the lapse of 24 hours in the case of addition of the crude emulsifier. Further, the mixture of the crude emulsifier and astaxanthin was allowed to stand at room temperature for 1 week; no aggregate precipitation was observed.

(3) In the Case of β-Carotene, Vitamin A, Vitamin E, Vitamin K1 and Coenzyme Q10 Being Used as Liposoluble Substances A 100-µl portion of the above crude emulsifiers C, D or E was added to 0.9 ml of 10-mM potassium-phosphate buffer (pH 7.0), and the mixture was further added to 10 mg of β-carotene (product of Nacalai Tesque, Inc.), vitamin A (product of Nacalai Tesque, Inc.), vitamin E (product of Nacalai Tesque, Inc.), vitamin K1 (product of Nacalai Tesque, Inc.) and coenzyme Q10, respectively, and each mixture was thoroughly mixed. As a result, each solid was dispersed in the liquid. In a control run in which water was used, each of these substances was found in a state floating on the liquid surface.

INDUSTRIAL APPLICABILITY

The present invention can provide a novel emulsifier which is highly safe and by itself shows high emulsifying property and high emulsifying stability. A water-soluble composition containing a liposoluble substance stably emulsified therein can be obtained using the emulsifier. Thus, the industrial contribution of the present invention is very great.

The invention claimed is:

1. An emulsifier comprising a fluid consisting essentially of a culture fluid, wherein the culture fluid comprises, as an active ingredient, a carbohydrate- and protein-based complex and the culture fluid is separated and recovered from a yeast culture obtained by cultivating a yeast for brewing, and wherein the carbohydrate- and protein-based complex has a molecular weight of not lower than 100,000 as determined by gel filtration.

2. A water-soluble composition comprising an emulsifier according to claim 1 and a liposoluble substance.

3. The composition according to claim 2, wherein the liposoluble substance comprises at least one species selected from among liposoluble drugs, vitamins, and fats and oils.

4. The composition according to claim 3, wherein the liposoluble drug is coenzyme Q10, the vitamin comprises at least one species selected from among vitamins A, D, E, and K, and derivatives thereof, and the fat or oil comprises at least one species selected from among essential oils, vegetable oils, animal oils, liposoluble colorants, perfumes, canthaxanthin, astaxanthin, zeaxanthin, lycopene, apocarotenal and β-carotene.

5. A method of producing a water-soluble composition comprising mixing an emulsifier according to claim 1 and a liposoluble substance with each other.

6. The production method according to claim 5, wherein the liposoluble substance comprises at least one species selected from among liposoluble drugs, vitamins, and fats and oils.

7. The production method according to claim 6, wherein the liposoluble drug is coenzyme Q10, the vitamin comprises at least one species selected from among vitamins A, D, E, and K, and derivatives thereof, and the fat or oil comprises at least one species selected from among essential oils, vegetable oils, animal oils, liposoluble colorants, perfumes, canthaxanthin, astaxanthin, zeaxanthin, lycopene, apocarotenal and β-carotene.

8. A method of producing an emulsifier comprising,
cultivating a yeast for brewing thereby producing a culture fluid and yeast, and
separating and recovering a carbohydrate- and protein-based complex fraction from the culture fluid, wherein the emulsifier comprises a fluid consisting essentially of the carbohydrate- and protein-based complex fraction having a molecular weight of not lower than 100,000 as determined by gel filtration.

9. An emulsifier comprising a fluid consisting essentially of a culture fluid, wherein the culture fluid comprises, as an active ingredient, a carbohydrate- and protein-based complex and the culture fluid is separated and recovered from a yeast culture obtained by cultivating a yeast for brewing, and wherein the yeast for brewing is *Candida sake* or *Saccharomyces sake*.

10. The emulsifier according to claim 9, wherein the *Candida sake* is *Candida sake* NBRC 1213 and the *Saccharomyces sake* is *Saccharomyces sake* Kyokai No. 10.

11. The emulsifier according to claim 9 or claim 10, wherein the carbohydrate- and protein-based complex has a molecular weight of not lower than 100,000 as determined by gel filtration.

12. A method of producing an emulsifier comprising,
cultivating a yeast for brewing thereby producing a culture fluid and yeast, and
separating and recovering a carbohydrate- and protein-based complex fraction from the culture fluid, wherein the yeast for brewing is *Candida sake* or *Saccharomyces sake*.

13. The method according to claim 12, wherein the *Candida sake* is *Candida sake* NBRC1213 and the *Saccharomyces sake* is *Saccharomyces sake* Kyokai No. 10.

* * * * *